United States Patent [19]

Danna et al.

[11] Patent Number: 4,539,586
[45] Date of Patent: Sep. 3, 1985

[54] CONNECTOR MODULE FOR VIDEO ENDOSCOPIC SYSTEM

[75] Inventors: Dominick Danna, Syracuse; Robert C. Wheeler, Skaneateles; Stanley R. English, Elbridge, all of N.Y.

[73] Assignee: Welch Allyn Inc., Skaneateles Falls, N.Y.

[21] Appl. No.: 539,982

[22] Filed: Oct. 7, 1983

[51] Int. Cl.³ .................. H04N 7/18; A61B 1/04; A61B 1/06
[52] U.S. Cl. .................. 358/98; 128/6; 350/96.18
[58] Field of Search .............. 358/98, 100; 128/4, 128/6, 303.15; 350/96.15, 96.18, 96.22; 339/16 R, 117 R, 117 P, 246

[56] References Cited

U.S. PATENT DOCUMENTS

| | | | |
|---|---|---|---|
| Re. 31,289 | 6/1983 | Moore | 128/6 |
| Re. 31,290 | 6/1983 | Moore | 128/6 |
| 4,074,306 | 2/1978 | Kakinuma | 358/1 |
| 4,253,448 | 3/1981 | Terada | 128/6 |
| 4,261,345 | 4/1981 | Yamaguchi | 128/6 |
| 4,303,301 | 12/1981 | Teichert | 350/96.22 |
| 4,402,313 | 9/1983 | Yabe | 128/6 |
| 4,491,865 | 1/1985 | Danna | 358/98 |
| 4,494,823 | 1/1984 | Yoshida | 350/96.18 |

*Primary Examiner*—Howard W. Britton
*Attorney, Agent, or Firm*—Bruns and Wall

[57] ABSTRACT

An interface module for a video endoscopic system that permits the insertion tube to be connected to and disconnected from a video processor quickly and easily whereby sterilizing the tube is simplified and the substitution of one tube for another is greatly facilitated. The connector module interfaces the various video and other electric connections and also interfaces a fiber optic bundle connection and a fluid supply connection between the processor and insertion tube. A solid state imaging device is located at the distal end of the insertion tube, and this device is driven by signals received from the processor and transmits video signals back to the processor. The interface module contains circuitry that accepts standard input signals from the processor for driving the imaging device, and this circuitry includes means for adjusting the input signals so that they are compatible with the particular imaging device in the tube. The interface module also contains circuitry for transmitting video output signals from the imaging device to the video processor. This transmission circuitry includes a video amplifier and means for adjusting the gain of the amplifier so that its output drives the video processing circuitry as required for optimum video performance.

20 Claims, 8 Drawing Figures

CONNECTOR MODULE FOR VIDEO ENDOSCOPIC SYSTEM

BACKGROUND OF THE INVENTION

This invention relates to a video endoscopic system and has particular reference to a novel interface module for releasably connecting the insertion tube of the system to the latter's video processor unit.

As explained in greater detail in reissued U.S. Pat. Nos. Re. 31,289 and Re. 31,290 to Moore et al, owned by the assignee of the instant invention, endoscopes can now be equipped with small video cameras that are able to be passed into confined regions heretofore inaccessible to this type of viewing equipment. The heart of the camera is a small solid state imaging device, sometimes referred to as a charge coupled device (CCD), that is able to record light images of a remote target and provide video signals indicative of the target information. A similar system is also disclosed in U.S. Pat. No. 4,074,306 to Kakinuma et al.

The video endoscopic system with which the present invention is concerned is essentially comprised of a video processor, a video monitor and a steerable insertion tube that enters the body cavity of the patient. Both the monitor and insertion tube are connected to the processor, and in prior developments it has not been possible to readily disconnect the tube from the processor due to the complexity of the electrical and mechanical connections between the two. This has made it awkward to sterilize the insertion tube and in addition has made it difficult to make the units interchangeable as is desirable.

SUMMARY OF THE INVENTION

The invention disclosed herein is primarily directed to an interface module that permits the insertion tube to be connected to and disconnected from the video processor quickly and easily. As a result, sterilizing the tube is simplified and the substitution of one tube for another is greatly facilitated. The connector module interfaces the various video and other electric connections, and also interfaces a fiber optic bundle connection and a fluid supply connection between the processor and insertion tube as will be described in more detail hereinafter.

The solid state imaging device mentioned above is located at the distal end of the insertion tube; it is driven by signals received from the processor and it transmits video signals back to the processor. The interface module contains circuitry that accepts standard input signals from the processor for driving the imaging device. However, there are small variations in the characteristics of different imaging devices and these must be compensated for so that uniform, high quality video performance is achieved. To this end, the circuitry in the module includes means for adjusting the input signals so that they are compatible with the particular imaging device in the tube.

The interface module also contains circuitry for transmitting video output signals from the imaging device to the video processing circuitry in the processor. This video signal transmission circuitry includes a video amplifier and means for adjusting the gain of the amplifier so that its output drives the video processing circuitry as required for optimum video performance. The various circuit adjustments in the module permit different modules to be compatible with the processor regardless of minor variations in the characteristics of the particular imaging device in the module. This permits interchangeability of insertion tubes while at the same time ensuring uniform, high quality video performance.

DESCRIPTION OF THE PREFERRED EMBODIMENTS

Figure 1:
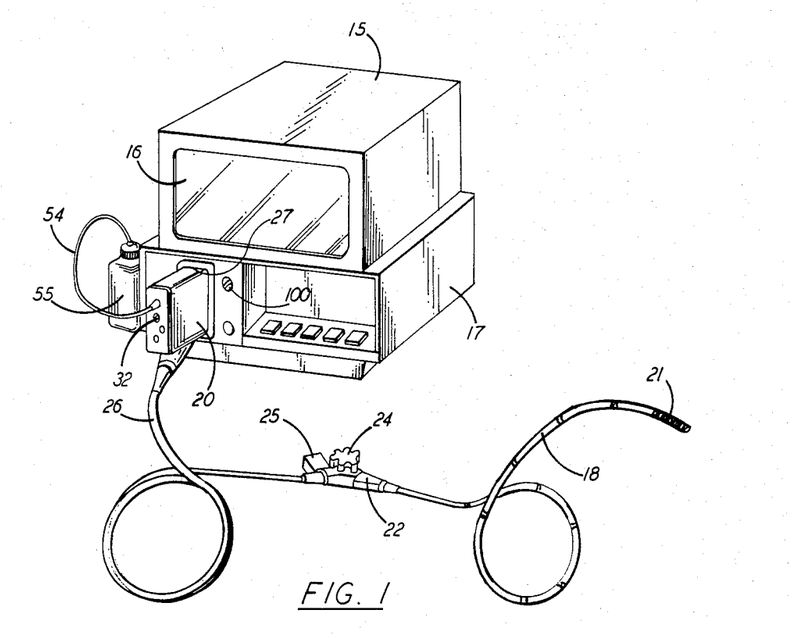
FIG. 1 is a front perspective view of a video endoscopic system embodying the invention.

Having reference now to the drawings, and with particular reference to FIG. 1, the video endoscopic system of which the present invention is a part is essentially comprised of a video monitor 15 having the usual screen 16, a video processor 17, an insertion tube 18 and an interface module 20 that releasably connects the insertion tube to the processor. The insertion tube is the portion of the apparatus that enters the body cavity of the patient and is flexible and steerable. At its distal end 21, the tube contains a known type of solid state imaging device such as a virtual phase charge coupled imaging device (not shown), and at its proximal end 22 the tube is provided with a steering control 24 and a valve control 25 for controlling the passage of air and water to the distal end of the tube. The insertion tube 18 is connected to the interface module 20 by an interface or extension cable 26, the latter having essentially the same construction as the tube except for the steering mechanism.

Figure 3:
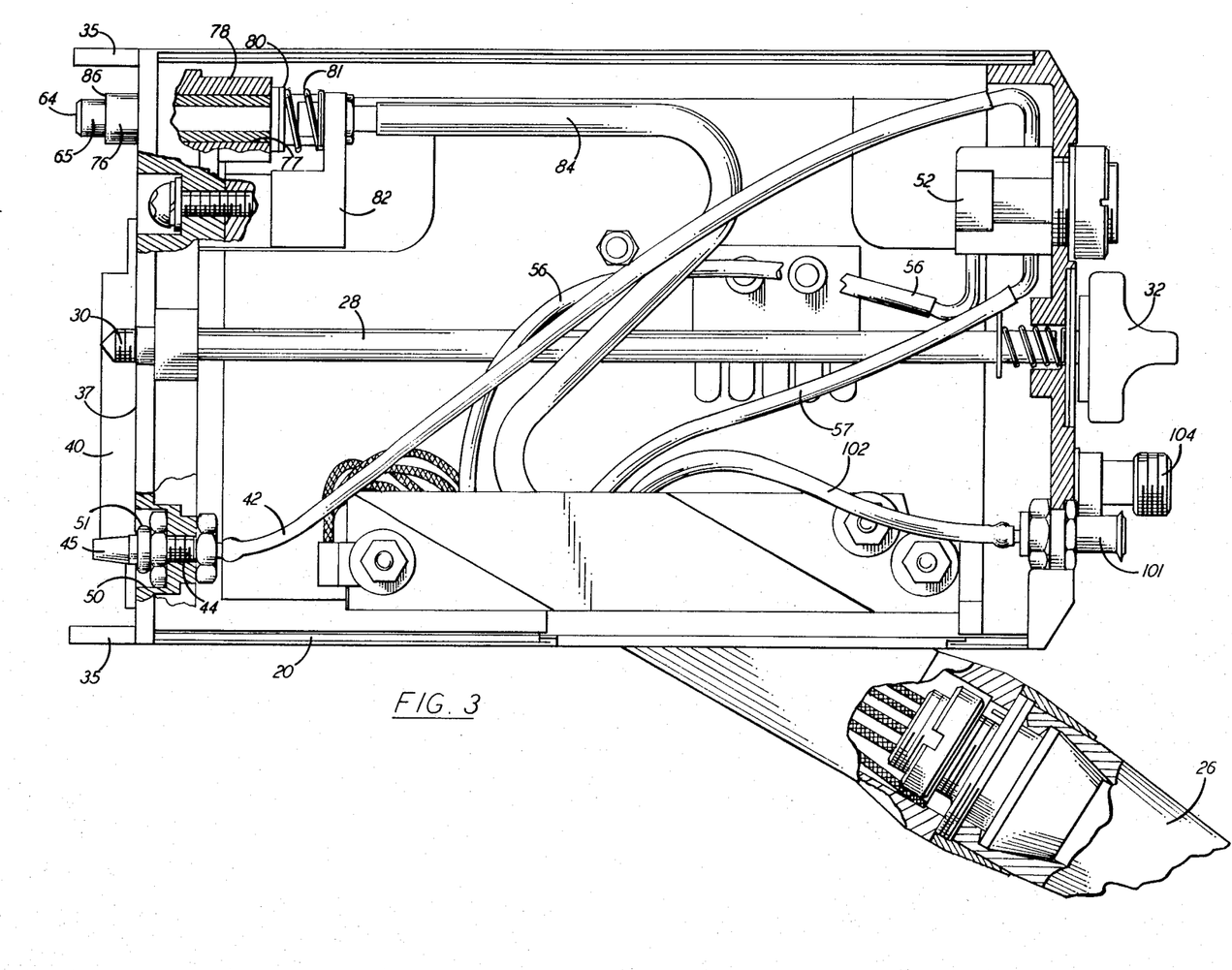
FIG. 3 is an enlarged side elevation of the interface module with the side wall removed and parts shown in section to illustrate certain details of the construction.
Figures 4, 6:
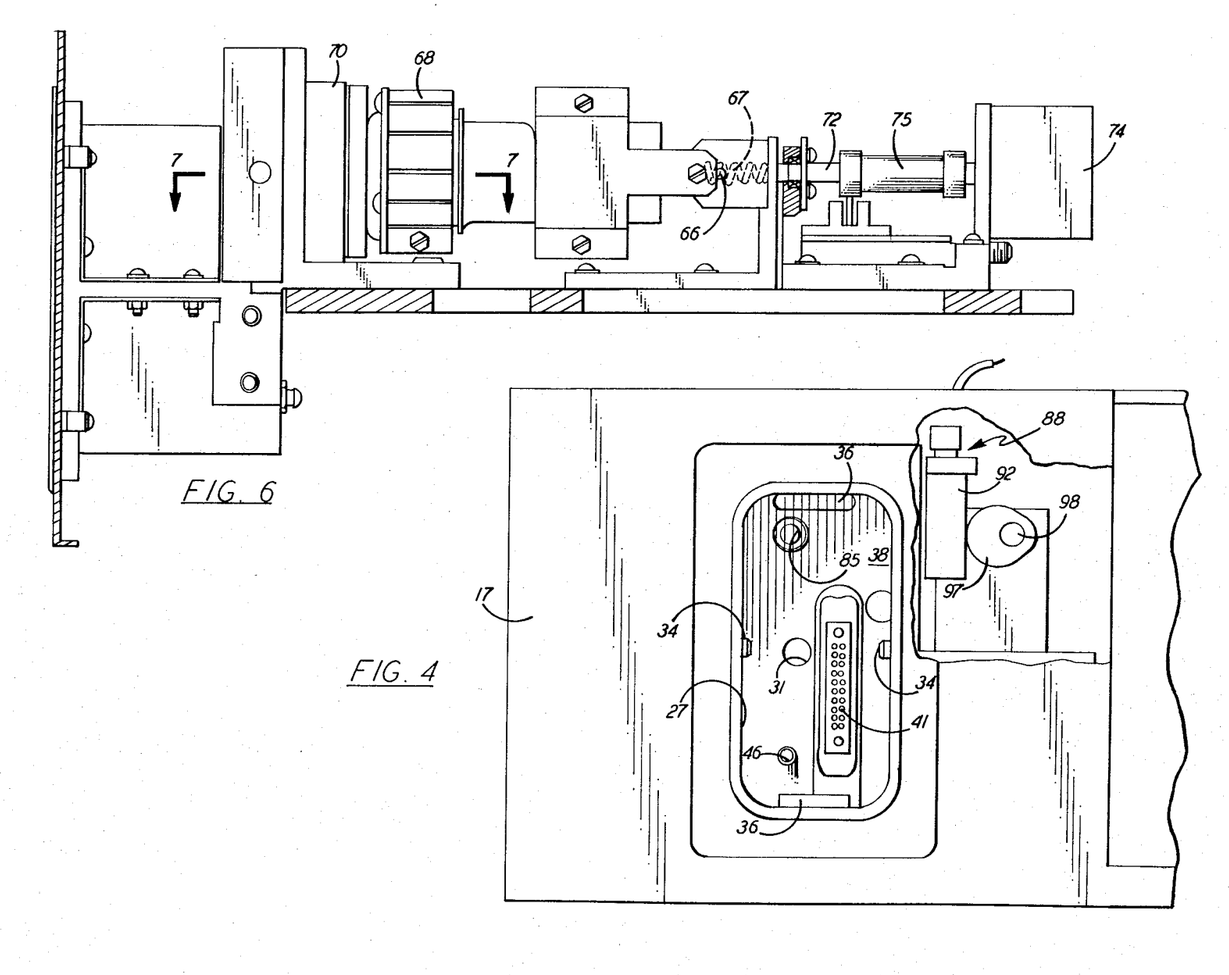
FIG. 4 is an enlarged, fragmentary front elevation of the processor.
FIG. 6 is an enlarged side elevation of the primary illumination source and motor and drive for the color wheel, both located in the processor.

The interface module 20 is a generally box-like receptacle the inner end of which is received with a sliding fit in a recess 27, FIGS. 1 and 4, in the front wall of the video processor 17. The function of the module is to make the various electrical and mechanical connections between the insertion tube and processor readily disconnectable whereby module and tube assemblies can be interchanged as, for example, when a tube must be sterilized after use. To this end, the module is releasably connected to the processor by a rod 28, FIG. 3, that extends longitudinally through the module as shown and terminates at its inner end in a double lead screw 30. The screw 30 is received in a mating bore 31 in the processor, FIGS. 4 and 5, and the threaded engagement is effected by a knob 32 at the outer, exposed end of the module.

The module 20 is guided into the processor recess 27 by guide rails 34, FIG. 4, in the recess that are received in conforming channels (not shown) in the module and also by upper and lower guide tabs 35, FIG. 3, that project from the inner end of the module and are received in mating recesses 36 in the processor, FIG. 4. The module lead screw 30 is threaded into the bore 31 until the inner end wall 37 of the module abuts firmly against the back wall 38 of the processor recess, FIGS. 3, 4 and 5. This close contact between the walls 37 and 38 is important in making the proper electrical and mechanical connections to be described.

When the module 20 is connected to the processor as above described, the electrical connections are made by the engagement of a female plug 40, FIG. 3, on the end wall of the module with a male plug 41 in the back wall of processor recess, FIG. 4. At the same time, a connection is made for bringing low pressure air to an air supply conduit 42 in the module, see FIG. 3.

Figure 5:
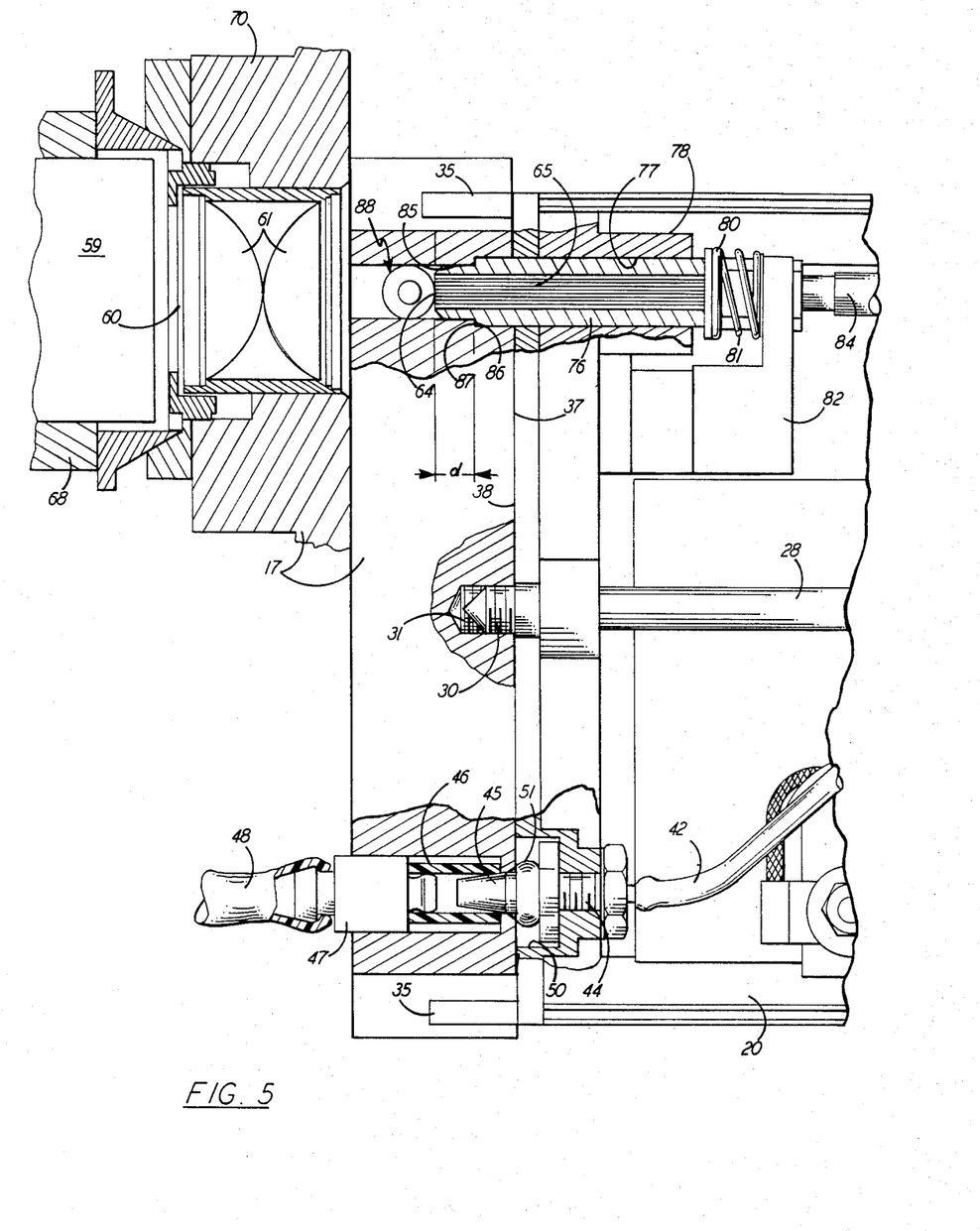
FIG. 5 is an enlarged vertical sectional view of the interface between the interface module and processor with parts shown in section to illustrate certain details of the construction.

The conduit 42 is connected at one end to a fitting 44 in the end wall 37 of the module, and this fitting has an outwardly projecting nipple 45 that is received with an airtight wedge fit in a resilient hose 46, FIG. 5, in the processor. The hose 46 is connected to one end of a fitting 47 the other end of which is connected to a conduit 48 leading to a pump (not shown) in the processor.

The fitting 44 passes through a recess 50 in the end wall 37 of the module and in this recess it is encircled by a resilient gasket 51. When the module is connected to the processor with their respective walls 37 and 38 in contact with one another, the gasket 51 is squeezed against the processor wall 38 to ensure an airtight air supply connection.

The air supply conduit 42 in the module is connected at its opposite end to a valve 52, FIG. 3, that is controlled by the valve control 25, FIG. 1, at the proximal end of the insertion tube. The valve 52 has an external connection to a conduit 54 that is connected at its other end to a water jar 55 suitably mounted on the outside of the processor as shown in FIG. 1. Inside the module, the valve 52 is connected to a water conduit 56, FIG. 3, and a second air conduit 57 both of which lead into the extension cable 26. The air is used to charge the water jar 55 and the valve control 25, which is not per se a part of the present invention, can be operated so that air alone, water alone or air and water intermittently can be delivered to the distal end of the insertion tube to cleanse the end face thereof.

When the interface module 20 is connected to the processor an illumination connection is also made whereby light from a light source in the processor is transmitted by a fiber optic bundle to the distal end of the insertion tube. The light source is an arc lamp 59, FIGS. 5, 6 and 7, and the light rays emitted by the lamp pass through a filter 60 and a lens system 61 which focuses the rays at a point 62 as indicated by the light ray lines 63 in FIG. 7. At or very near the focal point 62, the light enters the light receiving end 64 of a fiber optic bundle 65 that projects from the module end wall 37 as will be described in greater detail below.

Figure 7:
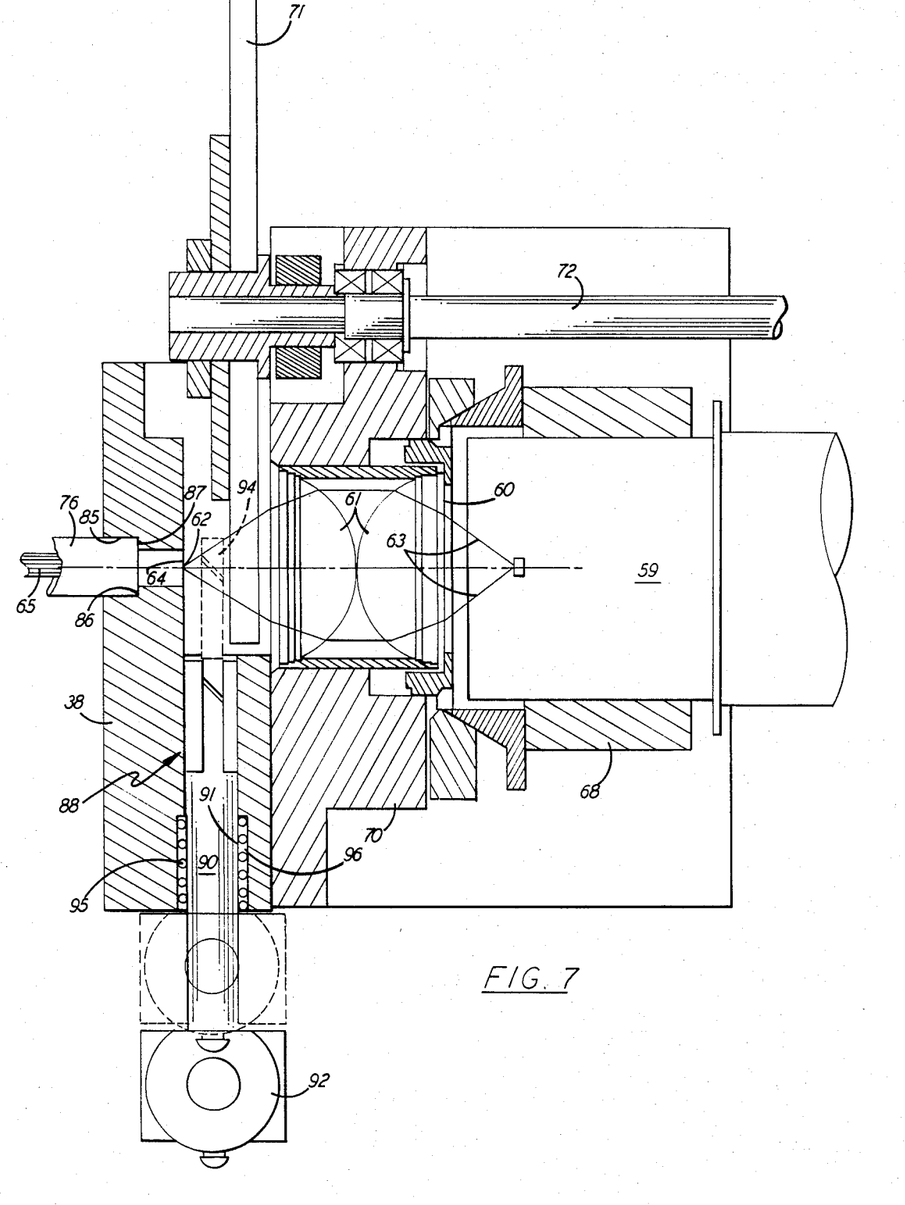
FIG. 7 is an enlarged horizontal sectional view through the illumination system taken substantially on line 7—7 of FIG. 6.

The arc lamp 59 is mounted in the processor so that it has limited axial movement due to a pin and slot connection at 66, FIG. 6. Compression springs 67 at this connection normally urge the front end of the lamp housing 68 into engagement with the housing 70 for the lens system as best shown in FIGS. 5 and 7. If, however, it becomes necessary to replace a lamp, the lamp housing and associated parts can be moved back against the action of the springs, FIG. 6, and then tilted upwardly to effect the replacement.

The light rays emitted by the lamp 59 also pass through a color wheel 71, FIG. 7, that is mounted on a shaft 72 driven by a stepping motor 74, the motor shaft being connected to the color wheel shaft 72 by a flexible coupling 75. The construction of the color wheel and the manner in which it coacts with the arc lamp are known in the art.

In the light transmitting fiber optic bundle 65 referred to above, the fibers that project through the end wall 37 of the module, FIG. 3, are encased in a rigid sleeve 76 that is slidably mounted in a horizontal bore 77 in a boss 78 on the inside of the end wall. Outward movement of the sleeve 76 is limited by a collar 80 on the sleeve, the collar being urged into engagement with the boss by a compression spring 81 that encircles the sleeve between the collar and a support bracket 82. Inwardly of the bracket 82, within the module, the fibers of the bundle are loose and are encased in a flexible sheath 84. This portion of the bundle extends through the extension cable 26 and insertion tube 18 to the distal end thereof.

The portion of the fiber optic bundle sleeve 76, FIG. 5, that projects beyond the module end wall 37 is received with a sliding fit in a bore 85 in the processor wall 38. In order to position the light receiving end 64 of the bundle as close as possible to the focal point 62 of the lamp, sleeve 76 is formed with an annular shoulder 86 that engages a corresponding shoulder 87 in the bore 85. With this arrangement, if the distance d, FIG. 5, from the sleeve shoulder 86 to the end of the bundle is made equal to the length of the reduced diameter portion of bore 85, the light receiving end of the bundle will always be positioned at or very near the focal point. If the sleeve 76 otherwise projects too far beyond module end wall 37, the sleeve will be pushed back in the module against the action of spring 81 as best shown in FIG. 5.

Against the possibility of a failure in the arc lamp illumination system when the video endoscopic system is in use, a secondary or back-up light source is provided which is indicated generally at 88 in FIGS. 4, 5 and 7. The back-up source includes a horizontally disposed hollow cylinder 90, FIG. 7, that is slidably mounted in a bore 91 in the processor and contains a fiber optic bundle (not shown). The cylinder 90 is connected at its outer end to a vertically disposed cylinder or tube 92, FIGS. 4 and 7, that contains a conventional filament lamp (not shown). The light rays from the lamp are directed into the outer end of the fiber bundle which transmits them to its inner end from which they are directed onto a 45° mirror 94; the mirror directs the light into the light receiving end 64 of the fiber optic bundle 65 when the back-up light source is in its operative position as shown in phantom lines in FIG. 7.

Figure 2:
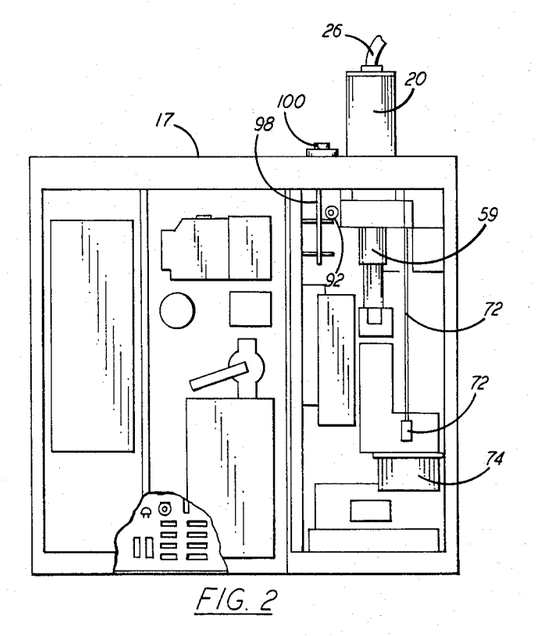
FIG. 2 is an enlarged top plan view of the video processor and interface module, the top cover of the processor having been removed.

The back-up light source 88 is normally maintained in inoperative position, as shown in solid lines in FIG. 7, by a compression spring 95 located in a counterbore 96. The light source can be moved into operative position, against the action of this spring, by a cam 97 mounted on a shaft 98, FIGS. 2 and 4. The cam shaft 98 has an operating knob 100, FIGS. 1 and 2, at the front of the processor. In FIG. 4, the cam has been rotated to move the back-up light source into its operative position.

Referring once again to FIG. 3, the outer, exposed end of the module 20 has a fitting 101 for connecting the module to a source of inert gas that may be required for insulflation. Inside the module, this fitting is connected to a conduit 102 that communicates with the extension cable 26 and insertion tube 18 so that gas can be delivered to the distal end of the latter. The outer end of the module also has a fitting 104 for the attachment of a safety ground wire which is not a part of the present invention.

The solid state imaging device located at the distal end of the insertion tube 18 is driven by signals received from the processor and it transmits video signals back to the processor. These signals are transmitted between the processor and module through the electrical connections 40 and 41, FIGS. 3 and 4. The module contains circuitry, shown in a schematic and greatly over-simplified manner in FIG. 8, that accepts standard input signals from the processor for driving the imaging device. This circuitry includes a parallel clock driver circuit 105 and a serial clock driver circuit 106.

Because there are small differences in the characteristics of different imaging devices, it is necessary for the driver circuits to convert the standard input signals received from the processor to the correct signals for driving the particular imaging device in the insertion tube. Stated another way, variations in different imaging devices must be compensated for so that uniform, high quality video performance is achieved at all times.

Figure 8:
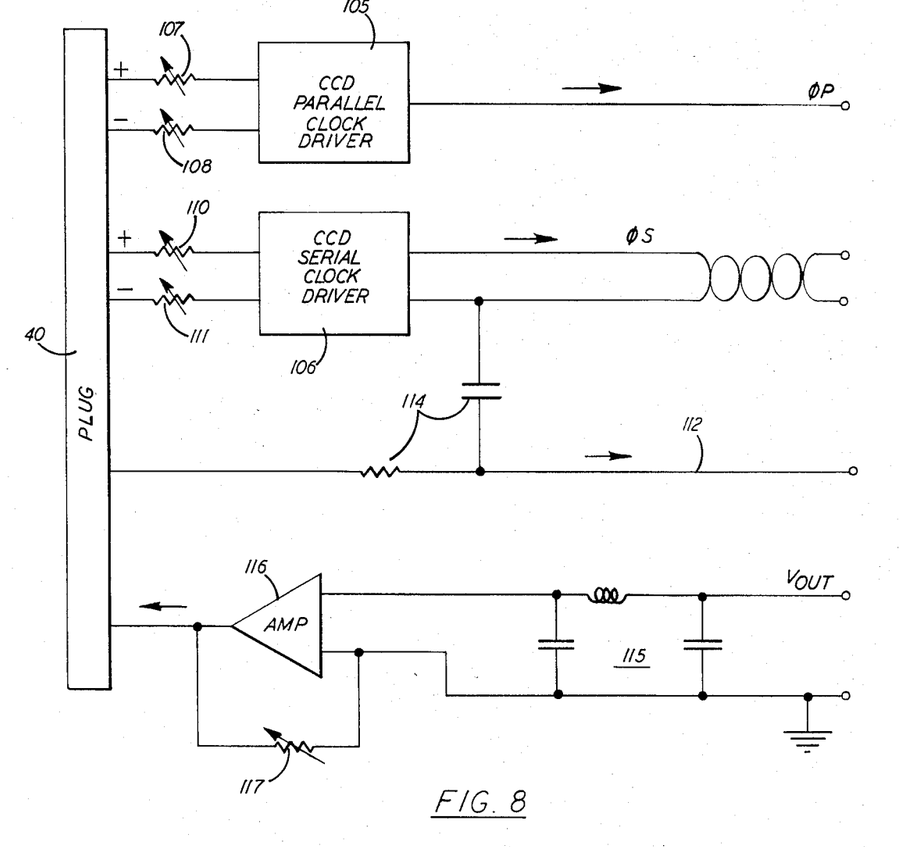
FIG. 8 is a schemmatic diagram illustrating the application of the circuit adjustments in the interface module.

The parallel clock driver circuit 105 converts the input signals it receives to the correct signals for its imaging device by adjustment means that permit independent adjustment of the parallel clock positive voltage excursion and the parallel clock negative voltage excursion. These adjustment means are shown in FIG. 8 as variable resistors 107 and 108, respectively, and resistor 107 enables the positive voltage excursion to be adjusted, for example, from −7 to +3.5 volts while resistor 108 enables the negative voltage excursion to be adjusted from −10 to −21.5 volts by way of example. In this connection, the parallel clock driver circuit has a low output impedance capable of properly matching and driving the long drive line to the imaging device.

The serial clock driver circuit 106 converts the input signals it receives to the correct signals for the imaging device by means of variable resistors 110 and 111 that permit independent adjustment of the serial clock positive voltage excursion and serial clock negative voltage excursion respectively. Resistor 110 enables the positive voltage excursion to be adjusted from −7 to +7 volts, and resistor 111 enables the negative voltage excursion to be adjusted from −10 to −21.5 volts.

In the FIG. 8 schematic, power is supplied to the imaging device by the VDD line 112 in connection with an RC decoupling filter 114. The video output signals from the imaging device are transmitted to the video processor by circuitry including a filter 115 and a video amplifier 116. Filter 115 filters undesired 7.16 MHZ serial clock feed through from the video output signals. The amplifier 116 has gain adjustment means shown as a variable resistor 117. The amplifier gain is adjusted in the module so that the amplifier has a low impedance output that drives the video processor circuitry as required for optimum video performance.

The five module circuit adjustments described above are an important feature of the invention in that they permit different modules to be compatible with the processor regardless of minor variations in the characteristics of the particular imaging device in the module.

From the foregoing description it will be apparent that the invention disclosed herein provides a novel and very advantageous interface module that permits the insertion tube of a video endoscopic system to be connected to and disconnected from the video processor quickly and easily. As a result, sterilizing the tube is simplified and the substitution of one tube for another is greatly facilitated. As will be understood by those familiar with the art, the invention may be embodied in other specific forms without departing from the spirit or essential characteristics thereof.

We claim:

1. In a video endoscopic system including a video processor having an illumination source, a video monitor connected to the processor, and an insertion tube having a solid state imaging device at its distal end; the improvement comprising an interface module for releasably connecting the insertion tube to the processor, the proximal end of the insertion tube being operatively connected to the module, first coacting means in the module and processor for releasably securing the former to the latter, a fiber optic bundle in the module for transmitting light through the insertion tube to the distal end thereof, second coacting means in the module and processor for positioning the light receiving end face of the bundle at the focal point of the illumination source when the module and processor are secured together, an air supply conduit in the module for delivering air to the insertion tube, third coacting means in the module and processor for connecting the conduit in a sealed manner to an air supply conduit in the processor when the module and processor are secured together, and coacting electrical connector means on the module and processor that operate to connect circuitry in the module with circuitry in the processor when the module and processor are secured together.

2. A video endoscopic system as defined in claim 1 wherein the first coacting means for releasably securing the module to the processor comprises a multiple lead screw in the module and a conforming threaded bore in the processor.

3. A video endoscopic system as defined in claim 2 together with an electrical interlock that coacts with the lead screw and bore to prevent an electrical connection between the processor and module before the screw and bore are engaged.

4. A video endoscopic system as defined in claim 1 together with a source of water mounted on the processor, conduit means connecting the water source with the air supply conduit in the module, and valve means operatively connected to the air and water conduits whereby air alone, water alone or air and water intermittently can be delivered to the distal end of the insertion tube.

5. A video endoscopic system as defined in claim 1 together with an inert gas supply conduit in the module for delivering gas to the insertion tube for insufflation purposes, and means on the exterior of the module for connecting the gas supply conduit with an inert gas source.

6. In a video endoscopic system including a video processor having an illumination source, a video monitor connected to the processor, and an insertion tube having a solid state imaging device at its distal end; the improvement comprising an interface module for releasably connecting the insertion tube to the processor, the proximal end of the insertion tube being operatively connected to the module, first coacting means in the module and processor for releasably securing the former to the latter, a fiber optic bundle in the module for transmitting light through the insertion tube to the distal end thereof, second coacting means in the module and processor for positioning the light receiving end face of the bundle at the focal point of the illumination source when the module and processor are secured together, and coacting electrical connector means on the module and processor that interengage to connect circuitry in the module with circuitry in the processor when the module and processor are secured together.

7. A video endoscopic system as defined in claim 6 wherein the first coacting means for releasably securing the module to the processor comprises a double lead screw in the module and a conforming threaded bore in the processor.

8. A video encoscopic system as defined in claim 7 together with an electrical interlock that coacts with the lead screw and bore to prevent an electrical connection between the processor and module before the screw and bore are engaged.

9. In a video endoscopic system including a video processor having an illumination source, a video monitor connected to the processor, and an insertion tube having a solid state imaging device at its distal end; the improvement comprising an interface module for releasably connecting the insertion tube to the processor, the proximal end of the insertion tube being operatively connected to the module, first coacting means in the module and processor for releasably securing the former to the latter, a fiber optic bundle in the module for transmitting light through the insertion tube to the distal end thereof, second coacting means in the module and processor for positioning the light receiving end face of the bundle substantially at the focal point of the illumination source when the module and processor are secured together, an air supply conduit in the module for delivering air to the insertion tube, and third coacting means in the module and processor for connecting the conduit in a sealed manner to an air supply conduit in the processor when the module and processor are secured together.

10. A video endoscopic system as defined in claim 9 wherein the first coacting means for releasably securing the module to the processor comprises a multiple lead screw in the module and a conforming threaded bore in the processor.

11. A video endoscopic system as defined in claim 9 together with a source of water mounted on the processor, conduit means connecting the water source with the air supply conduit in the module, and valve means operatively connected to the air and water conduits whereby air alone, water alone or air and water intermittently can be delivered to the distal end of the insertion tube.

12. In a video endoscopic system including a video processor having an illumination source, a video monitor connected to the processor, and an insertion tube having a solid state imaging device at its distal end; the improvement comprising an interface module for releasably connecting the insertion tube to the processor, the proximal end of the insertion tube being operatively connected to the module, first coacting means in the module and processor for releasably securing the former to the latter, the illumination source having a primary and a secondary light source, the secondary light source being a back-up source and being movable between inoperable and operable positions, the secondary light source normally being positioned in its inoperable position, a fiber optic bundle in the module for transmitting light through the insertion tube to the distal end thereof, and second coacting means in the module and processor for positioning the light receiving end face of the bundle at the focal point of the primary light source when the module and processor are secured together.

13. A video endoscopic system as defined in claim 12 together with means accessible from the exterior of the module for moving the secondary light source into and out of its operable position.

14. In a video endoscopic system having a video monitor, a video processor and illumination source, and an insertion tube having a solid state imaging device at its distal end; the improvement comprising an interface module for releasably connecting the insertion tube to the processor, the proximal end of the insertion tube being operatively connected to the module, circuitry in the module that accepts from the processor standard input signals for driving the solid state imaging device, and means forming a part of the circuitry for adjusting the input signals so that they are at the levels required to drive the particular imaging device in the insertion tube so that optimum video performance is achieved.

15. A video endoscopic system as defined in claim 14 wherein the solid state imaging device is a virtual phase charge coupled imaging device.

16. A video endoscopic system as defined in claim 15 wherein the circuitry in the module that accepts input signals from the processor includes a parallel clock driver circuit and a serial clock driver circuit.

17. A video endoscopic system as defined in claim 16 wherein the means for adjusting the input signals includes components for independently adjusting the parallel clock positive and negative voltage excursions.

18. A video endoscopic system as defined in claim 16 wherein the means for adjusting the input signals includes components for independently adjusting the serial clock positive and negative voltage excursions.

19. In a video endoscopic system having a video monitor, a video processor and illumination source, the processor including video processor circuitry, and an insertion tube having a solid state imaging device at its distal end; the improvement comprising an interface module for releasably connecting the insertion tube to the processor, the proximal end of the insertion tube being operatively connected to the module, circuitry in the module for transmitting video output signals from the solid state imaging device to the video processor circuitry in the processor, the video signal transmission circuitry including a video amplifier, and means for adjusting the gain of the amplifier so that its output drives the video processor in the manner required for optimum video performance.

20. In a video endoscopic system having a video monitor, a video processor and illumination source, the processor including video processor circuitry, and an insertion tube having a solid state imaging device at its distal end; the improvement comprising an interface module for releasably connecting the insertion tube to the processor, the proximal end of the insertion tube being operatively connected to the module, circuitry in the module that accepts from the processor standard input signals for driving the solid state imaging device, means forming a part of the circuitry for adjusting the input signals so that they are at the levels required to drive the particular imaging device in the insertion tube so that optimum video performance is achieved, and additional circuitry in the module for transmitting video output signals from the solid state imaging device to the video processor circuitry in the processor, the last-named circuitry including a video amplifier and means for adjusting the amplifier gain so that the amplifier has a low impedance output that drives the video processor in the manner required for optimum video performance.

* * * * *